US008833366B2

(12) United States Patent
Colombo et al.

(10) Patent No.: US 8,833,366 B2
(45) Date of Patent: Sep. 16, 2014

(54) LIQUID-EVAPORATE DELIVERY DEVICE

(75) Inventors: Joseph G. Colombo, Hackensack, NJ (US); Anthony J. Leardi, Monroe, NY (US); John E. Lando, Wayne, NJ (US)

(73) Assignee: Takasago International Corporation, Tokyo (JP)

( * ) Notice: Subject to any disclaimer, the term of this patent is extended or adjusted under 35 U.S.C. 154(b) by 1203 days.

(21) Appl. No.: 12/645,262

(22) Filed: Dec. 22, 2009

(65) Prior Publication Data

US 2010/0269826 A1 Oct. 28, 2010

Related U.S. Application Data

(63) Continuation of application No. PCT/US2008/069176, filed on Jul. 3, 2008.

(60) Provisional application No. 60/947,830, filed on Jul. 3, 2007, provisional application No. 60/948,505, filed on Jul. 9, 2007.

(51) Int. Cl.

| | |
|---|---|
| *A61M 15/00* | (2006.01) |
| *A61M 16/00* | (2006.01) |
| *A61L 9/12* | (2006.01) |
| *A61L 9/03* | (2006.01) |
| *A01M 1/20* | (2006.01) |

(52) U.S. Cl.

CPC ................. *A61L 9/037* (2013.01); *A61L 9/122* (2013.01); *A61L 9/127* (2013.01); *A01M 1/2044* (2013.01); *A01M 1/2033* (2013.01)

USPC ............. 128/204.13; 128/203.12; 128/200.14

(58) Field of Classification Search
CPC . A61M 16/18; A61M 16/183; A61M 16/186; A61M 16/104; A61M 16/16; A61M 15/00; A61M 15/08; A61M 11/06; B05B 7/0012; A61L 9/127; A61L 9/04
USPC ............. 128/204.13, 200.14, 200.17, 200.18, 128/200.11, 200.21, 200.22, 200.24, 128/203.12, 204.14; 206/570
See application file for complete search history.

(56) References Cited

U.S. PATENT DOCUMENTS

| | | | | |
|---|---|---|---|---|
| 1,984,055 | A | 12/1934 | Carter | |
| 4,396,557 | A * | 8/1983 | DeLuca | 261/30 |
| 4,968,487 | A * | 11/1990 | Yamamoto et al. | 422/125 |
| 6,371,450 | B1 | 4/2002 | Davis et al. | |
| 7,093,949 | B2 | 8/2006 | Hart et al. | |
| 7,499,632 | B2 * | 3/2009 | Granger et al. | 392/386 |
| 7,744,833 | B2 * | 6/2010 | Varanasi et al. | 422/306 |
| 7,775,459 | B2 * | 8/2010 | Martens et al. | 239/102.2 |
| 8,074,640 | B2 * | 12/2011 | Davies et al. | 128/200.14 |
| 2004/0265189 | A1 * | 12/2004 | Schwarz | 422/124 |
| 2005/0265904 | A1 * | 12/2005 | Hardy et al. | 422/123 |

OTHER PUBLICATIONS

IPRP for PCT/US2008/069176 Jan. 14, 2010.
Written Opinion for PCT/US2008/069176 Sep. 30, 2008.
International Search Report for PCT/US08/069176, Sep. 20, 2008.

* cited by examiner

*Primary Examiner* — Justine Yu
*Assistant Examiner* — Colin W Stuart
(74) *Attorney, Agent, or Firm* — Baker Botts L.L.P.

(57) ABSTRACT

The present application relates to a liquid-evaporate delivery device which relies on the efficient use of air currents to deliver liquid evaporate to airspace around the device. Efficient air currents may be provided by rotating the air currents around the wick, by providing a helical channel for the air to flow around the wick, and/or by aligning a fan with the longitudinal axis of the wick.

23 Claims, 12 Drawing Sheets

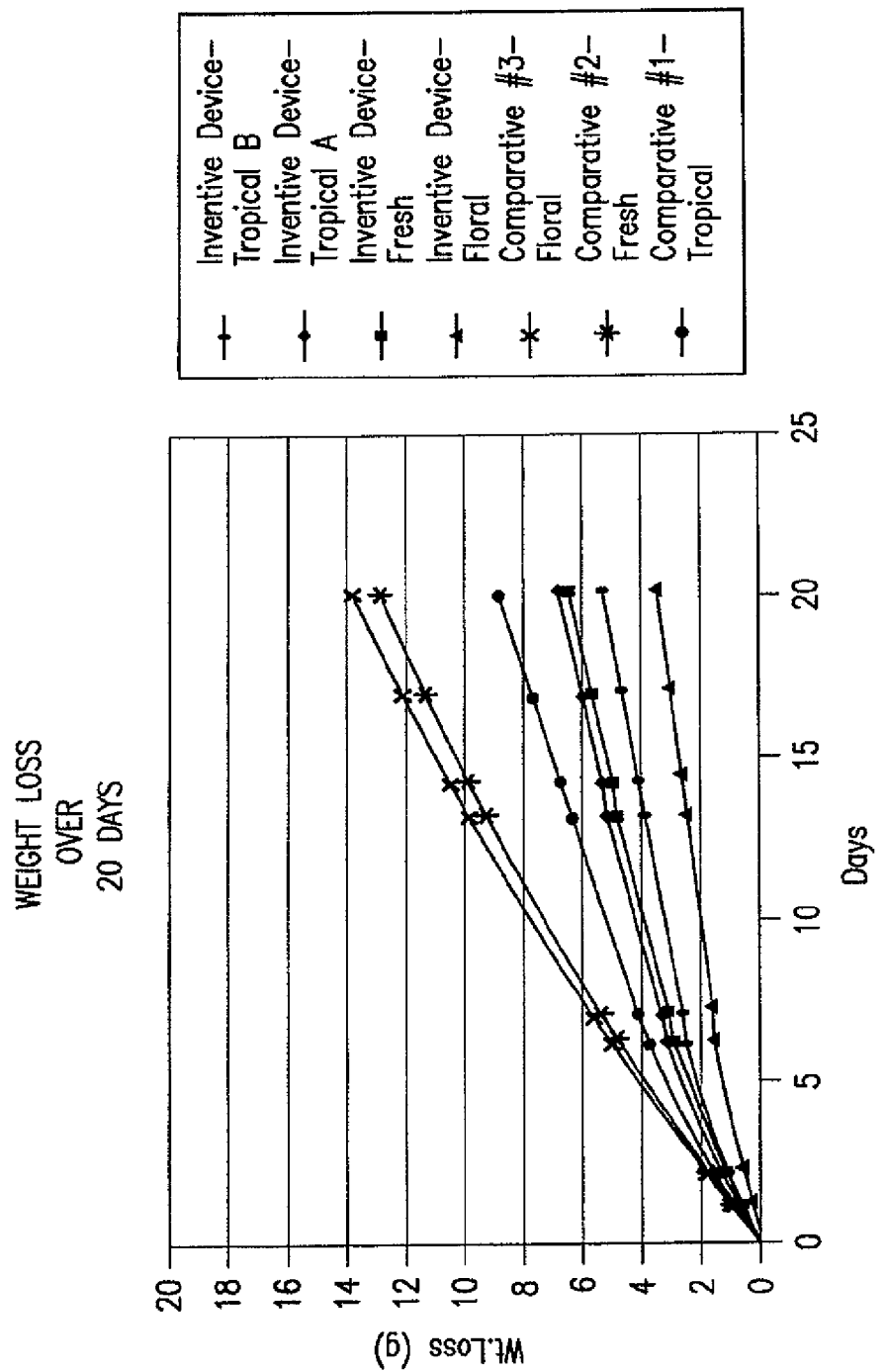

LIQUID-EVAPORATE DELIVERY DEVICE

CROSS REFERENCE TO RELATED APPLICATIONS

The present application is a continuation of International Application No. PCT/US2008/069176, filed Jul. 3, 2008, which claims the benefit of U.S. Application No. 60/947,830, filed Jul. 3, 2007 and U.S. Application No. 60/948,505, filed Jul. 9, 2007, each of which are hereby incorporated by reference in their entirety.

FIELD OF THE INVENTION

The present application provides a device that delivers evaporated liquids, such as vapors from a liquid fragrance composition, into the surrounding air space (e.g. place of commerce, interior of a car, or room in office or house).

BACKGROUND OF THE INVENTION

Complex liquid mixtures such as a fragrance or fragrance oils can be delivered to the air by a variety of methods. Exemplary devices which are known to deliver fragrance or fragrance oils include battery or plug-in air freshening devices that contain a fan and/or a heater to accelerate evaporation of the liquid. Such devices, however, have limitations such as inconsistent delivery rates and uneven and inefficient fragrance delivery.

For example, FIG. 1 illustrates an example of a prior art fragrance delivery device. This figure depicts the top view of a fragrance supply bottle and fan combination, within an enclosure, exhibiting less than ideal air flow. As denoted in letter C in FIG. 1, the fan supplies air to the wick without consideration of the air turbulence that exists in such a device, in which the fan and wick are oriented perpendicular to each other. Notice the excess air turbulence (FIG. 1, C) after the air strikes the wick and how the air flow turbulence continues beyond the wick. Also note that much of the air being supplied by the fan misses the wick, which is the area containing the highest fragrance concentration within the unit. Air deflects off the interior side of the enclosure causing further air flow disturbances (FIGS. 1, A and B). This air flow model representative of various prior art devices illustrates an inefficient fragrance delivery pattern because large amounts of fragrance is trapped within the enclosure and does not escape (see FIG. 1, A, B, C). Although weight loss may be significant, fragrance delivery into the surrounding air is marginal at best.

Without the use of air currents required to efficiently evaporate the liquid, devices have relied upon the application of heat. Unfortunately, certain notes of the fragrance compositions may be skewed by the heating element so that the full "bouquet" of the fragrance is not perceived by the subject, and the hedonic impression is diminished. The inefficient fragrance delivery pattern exhibited by prior art devices thus limits the creativity of the perfumer in selecting fragrances for the device. The perfumers may desire use of unique constituents with variable volatility, yet there are instances where a fragrance cannot be developed because the device requires the application of too much heat in order to deliver the vapors of the fragrance.

SUMMARY OF THE INVENTION

These design limitations and others are addressed by the liquid-evaporate delivery device of the present application.

One embodiment of the present invention provides a liquid-evaporate delivery device that includes a container containing a substance to be evaporated (preferably a liquid or gel substance); a wick having a first end, a second end and an exterior surface, the first end disposed within the bottle and the second end and exterior surface disposed exterior to the bottle; a device configured to impart an air flow on the wick (e.g. a fan); the device disposed below the bottle; and a housing, the bottle, heater element disposed within the housing. The air flow rotates around the exterior surface of the wick to provide an efficient means of delivering the liquid evaporate to the surrounding airspace, while avoiding or at least minimizing the requirement of a heating element.

Liquid that may be employed in the liquid-evaporate delivery device include fragrance compositions, insecticide or insect repellents. In specific embodiments the air flow that rotates around the wick is characterized as laminar, or substantially laminar, as opposed to a turbulent flow regime.

Another embodiment of the present application provides a liquid-evaporate delivery device in which the housing of the device includes at least one continuous baffle that defines a helical channel for directing the air flow around the exterior surface of the wick. The device may contain a single continuous baffle that defines a helical channel or alternatively be configured with multiple baffles that provide one or more helical channels. The size of the baffles may be determined by one of ordinary skill in the art, and may be constant or tapered within the device. The fan may be aligned, or substantially aligned with the longitudinal axis of the wick.

Another embodiment of the present application provides a liquid-evaporate delivery device comprising: (a) a retention member containing a substance or mixture of substances to be evaporated; (b) an evaporation member operatively engaged with the retention member; (c) a device configured to impart air flow on the evaporation member; (d) a housing, the retention member and fan disposed within the housing; wherein the housing includes at least one baffle that defines a helical channel for directing the air flow around the exterior surface of the wick.

The present application also provides methods of providing a room with a pleasing fragrance by using the liquid-evaporate device of the present application within that room. The present application also provides methods of providing a pleasing fragrance to car passengers, places of business and office space. Alternatively, the liquid-evaporate device of the present application can be used to deliver insect repellents or insecticides to spaces in which nuisance pests are a problem. The device may also be used to provide inhalation therapy to a subject in need thereof, by using, for example, an essential oil, or a therapeutic gel or liquid in the device in close proximity to the person receiving such inhalation therapy.

BRIEF DESCRIPTION OF THE DRAWINGS

FIG. 7 clearly shows that the longitudinal axis of the wick is aligned with the central axis of the fan.

FIG. 12 sets forth the average loss of fragrance over time using delivery devices of the present application.

DETAILED DESCRIPTION

Definitions

As used herein, the term "wick" refers to entities that absorbs a liquid and provides a surface area for liquid/air interaction to facilitate evaporation. The wick may be comprised of a material selected from, for example, a nylon, a linen, a felt, a rayon, a polyamide, a polymer such as polypropylene or polyethylene, polyester fibers, cellulose acetate fibers, ceramic, sintered glass, a plastic, a cotton, a cellulose or mixtures thereof.

As used herein, the term "substantially laminar air flow" refers to air flow characterized such that it has a Reynolds Number of below about 2500, preferably below about 2000, more preferably below about 1000. Details regarding determination of Reynolds Numbers can be found, for example, in Perry's Chemical Engineer's Handbook, 7th ed., which is hereby incorporated by reference.

As used herein, the wick is substantially aligned with the central axis of the fan when the central axis of the fan is within a small amount (e.g., ±10° or more preferably ±5° of parallel with the central axis of the wick.

Figure 1:
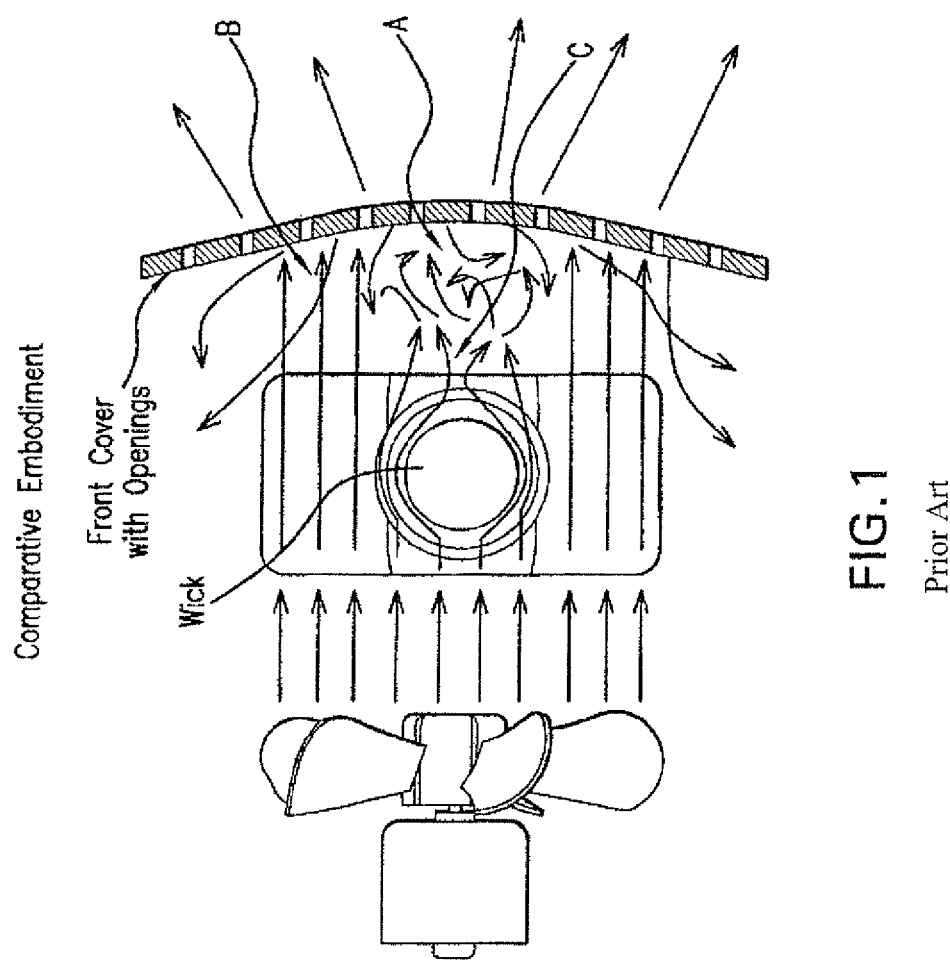
FIG. 1 is a comparative embodiment of the present application which shows the relatively inefficient use of air currents to evaporate a liquid from a wick.

As used herein, a "device configured to impart an air flow on the wick" refers to an entity or structure that provides sufficient air to a moist wick to facilitate evaporation under normal use conditions (e.g. room temperature and pressure). An example of a "device configured to impart an air flow on the wick" is a fan. In some delivery embodiments which, do not require the use of a fan to move air; the presence of an air intake vent is considered a "device configured to impart an air flow on the wick", provided that the air intake vent is positioned to achieve such a result. To one skilled in the art, there are numerous methods to deliver an air stream to the device.

As used herein "air flow rotates around the wick" is defined when the air flows around the exposed portion of the wick in a spiraling fashion. Due to the design of the liquid-evaporate delivery device of the present application, the air makes at least one complete revolution around the wick, preferably at least two or three revolutions around the exposed portion of the wick.

Embodiments of the Liquid-Evaporate Delivery Device

One embodiment of the present invention is shown in FIG. 2. The liquid-evaporate delivery device 1 shown in FIG. 2 has an option of operating by a plug-in power supply (not shown, discussed in detail below), or battery 9 for portable applications. The battery, via the control circuit board 7, supplies power to (impeller item 5 & DC motor item hereafter referred to as fan 6. The fan delivers air flow that rotates around the exterior surface of the wick, 13. In this embodiment, rotating air flow around the exterior surface of the wick is aided by helix or baffle 16 having a slight upgrade that forms a helical air channel 14.

The design of the helix or baffle 16 shown in FIG. 2 is such that the upper edge is approximately parallel to the base of the device, while the lower edge is slanted upward. Such a design allows air to move toward the center axis of the channel as it rotates around the wick. The baffle is preferably smooth to facilitate laminar air flow.

The aero-dynamic shape of liquid-evaporate delivery device, shown in FIG. 2 by enclosure items 2 and 3 assist in providing a unique helical channel 14 in the upper portion (FIG. 2, item 2) of the liquid-evaporate delivery device. This air flow model relies on the basic principal of evaporation, which is the process by which a liquid changes to a gas or vapor. The molecules in a liquid are constantly in motion, moving in all directions at different velocities. The molecules near the surface are the molecules that are released from the surface of the liquid into a gaseous state. This happens when those molecules collide into other molecules at high velocities. This process occurs more rapidly when temperature is increased because the molecules begin to move at higher velocities.

The operation of the present invention is unique in that the evaporation of the complex liquid mixture (e.g. fragrance or fragrance oil) off the wick 13, is more efficiently captured by the circulating airflow within the helical channel 14. As a result, more of the evaporation is propelled outward from the top of this aero-dynamic enclosure consisting of items 2 & 3 and introduced into the atmosphere, as compared to prior art devices that do not incorporate the helical channel (e.g. the device of FIG. 1). In FIG. 2, which may be designed to impart a hedonically pleasing fragrance to an air space (e.g. a room of a house); the fragrance 10 is carried by natural room air currents. It is understood that the device shown in the figures of the present application could deliver other evaporated liquids, such as insect or pest repellents or therapeutic gels and liquids (e.g. aromatherapy and a vaporizer for inhalation therapy for pharmaceutical applications). To one skilled in the art, other applications or configurations of this device could be envisioned.

The air supply enters the enclosure through air inlet 8 as shown in FIG. 2 and generated by the fan 6 and mounted within item 3 below the air tunnel 11, as illustrated in FIG. 2. The fan 6 is preferably mounted below the fragrance supply bottle 12 and bottle mount 4 so as to provide directed air upward through the enclosure, and is powered by a battery 9 or a plug-in power supply (not shown). In this illustration the battery 9 is shown for portable operation. The fan 6 may have more than one speed, which would permit the amount of fragrance delivered into the atmosphere to be controlled by adjusting the speed of the fan 6.

The purpose of the helical channel 14 is to direct the air flow, supplied by air inlet 8. Air is introduced into the air tunnel 11 through its lower openings and put into motion by the fan 6 and directionally guided upward by the air tunnel 11 leading into the helical channel 14, whereby developing into a helical air flow pattern around the wick 13, which comes up through the center of the helix, allowing the air flow to more efficiently capture evaporation.

An example of the air model employed by the liquid-evaporate delivery device of the present application is shown in FIG. 3, in which the evaporating liquid is efficiently captured by the circulating airflow within the helical channel 14. The air flow shown in the devices of the present invention capture the evaporated liquid much more efficiently than, for example, the liquid-evaporate delivery device shown in FIG.

1, in which the air currently can be seen to go in a multitude of different directions after coming into contact with the wick. Devices like the comparative device of FIG. 1 are more likely to require additional amounts of heat to facilitate evaporation.

Figure 3:
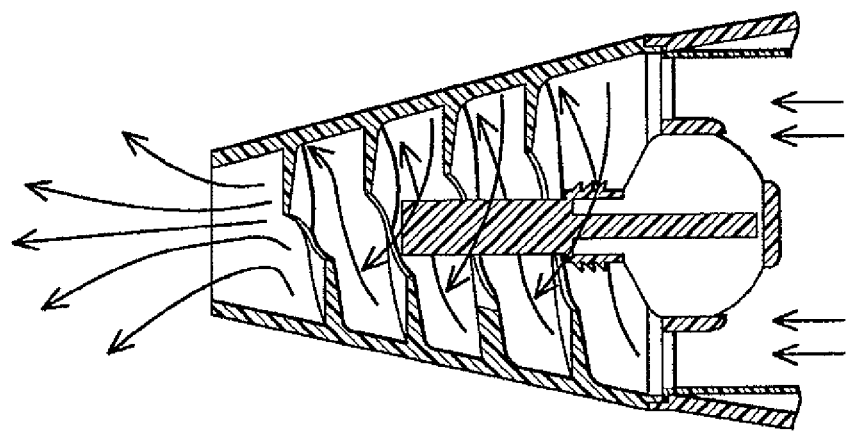
FIG. 3 provides a clear view of the air currents within the device, the air currents shown there to rotate around the wick.
Figure 4:
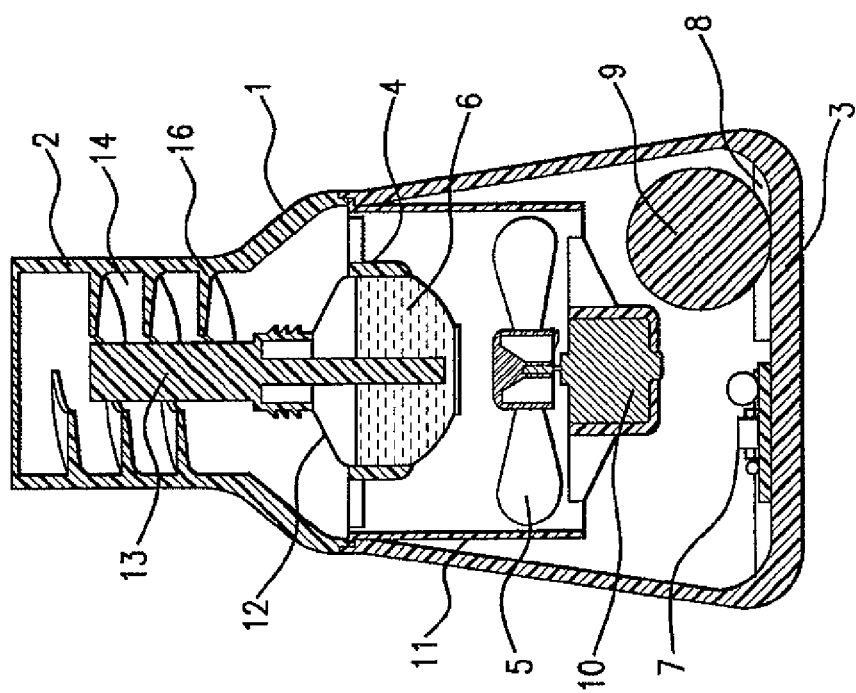
FIG. 4 demonstrates a "table-top" embodiment with a shape that differs slightly from the shape of the table-top embodiment of FIG. 2.
Figure 5:
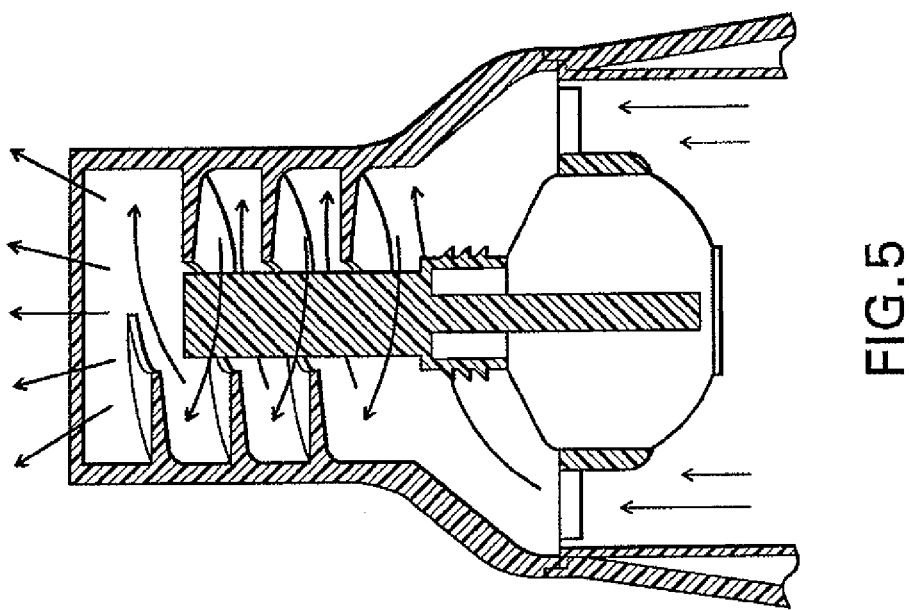
FIG. 5 provides a clear depiction of the air currents of a device similar to that of FIG. 4.
Figure 7:
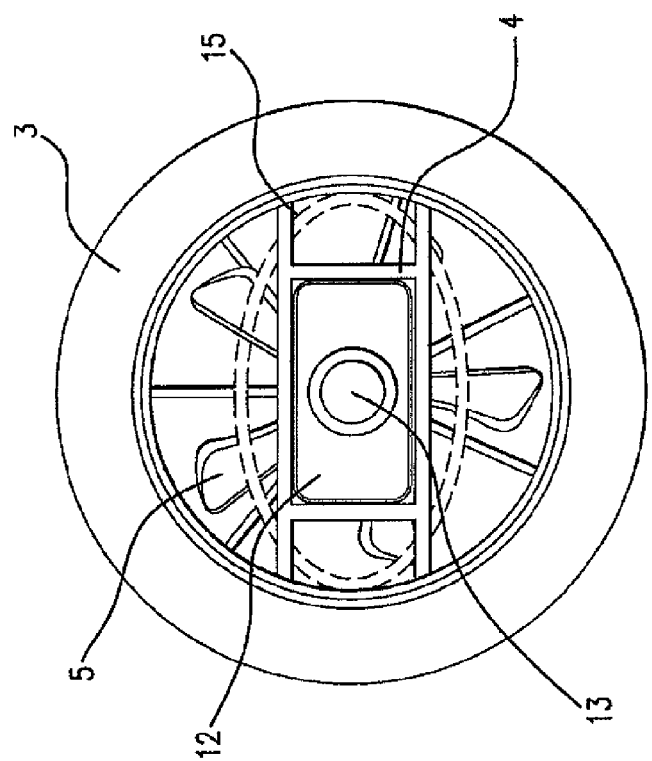
FIG. 7 provides a birds-eye view of the device shown in FIG. 6.

As shown in FIG. 7, the wick 13 is aligned, or at least substantially aligned with the central axis of the fan impeller, 5. This feature may be combined with a conical shape, shown in the liquid-evaporate delivery devices of FIG. 3. For comparison, FIGS. 4 and 5 demonstrate a liquid-evaporate delivery device in which the shape of the device around the wick is not conical. Nevertheless, the liquid-evaporate delivery device shown in FIGS. 4 and 5 provide efficient helical air flow by means of helix 16, oriented to provide a helical channel which efficiently delivers the evaporated liquid to the ambient air space surrounding the device.

Figure 6:
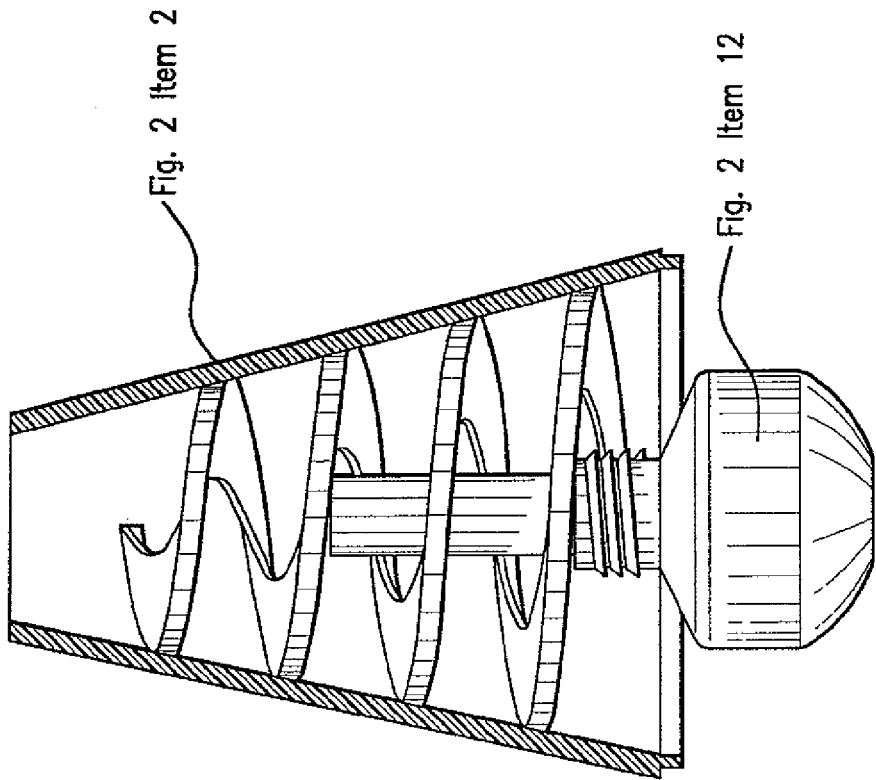
FIG. 6 demonstrates an alternative embodiment of the present invention, in which a helical channel is provided by a one-piece spiraling baffle design.

As described above, the liquid-evaporate delivery device may contain a baffle (see, for example, FIG. 2 or FIG. 6) that provides a helical air channel to efficiently delivery the evaporated liquid to the ambient air. In some embodiments, the liquid-evaporate delivery device contains a plurality of baffles, the baffles preferably oriented at a slight upgrade. For example, the baffles may be spaced about three inches apart. Alternatively, as shown in FIGS. 2 and 6, the helical air channel may be provided by a one-piece, spiraling baffle design.

Figure 2:
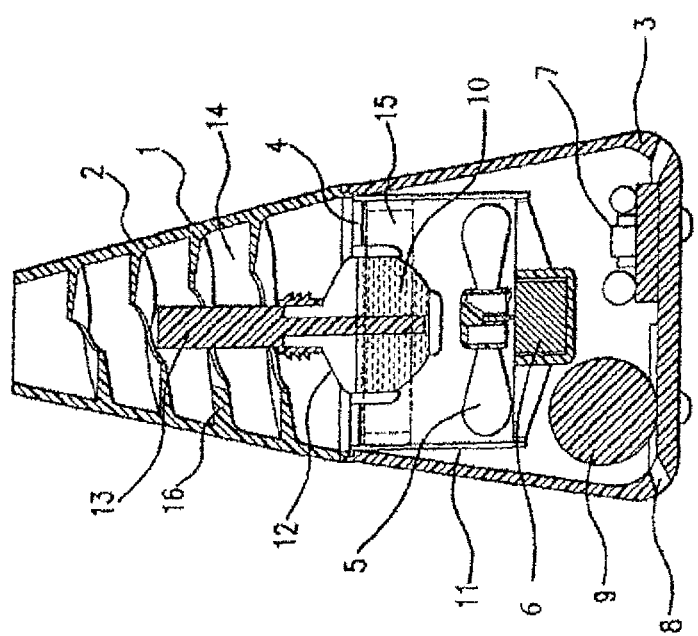
FIG. 2 is an example of a "table-top" embodiment of the device of the present invention that is powered by a battery.

Regardless of whether a plurality of baffles, or a one-piece, spiraling baffle design is employed, it has been found that the size of the outlet aperture, denoted as 18 in FIG. 2, is important to the functioning of the device. Accordingly, the person of ordinary skill in the art should exercise care in selecting the size of the outlet so that the rate of evaporation (e.g. the extent to which fragrance is released) is optimized based on the particular application for which the liquid-evaporate device is employed.

The liquid-evaporate delivery device of the present invention may be powered by a battery (e.g. battery 9 of FIG. 2). In alternative embodiments, the liquid-evaporate delivery device is adapted to be plugged into a wall socket by AC wall outlet, which powers the device and may replace the battery described above. In a further embodiment, the device may be configured for both battery and AC wall outlet plug-in operation.

Figure 8:
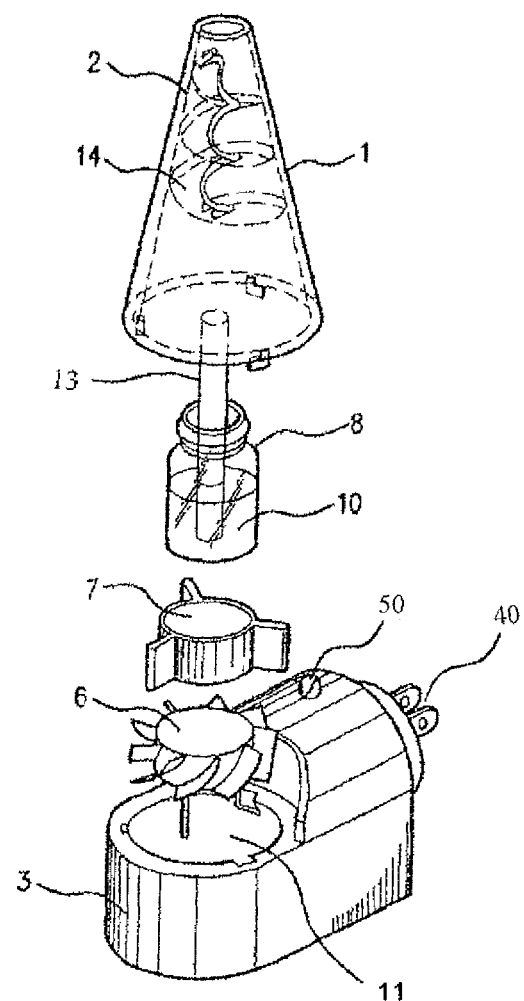
FIG. 8 is a picture of a "plug-in" version of a liquid-evaporate delivery device of the present invention.
Figure 9:
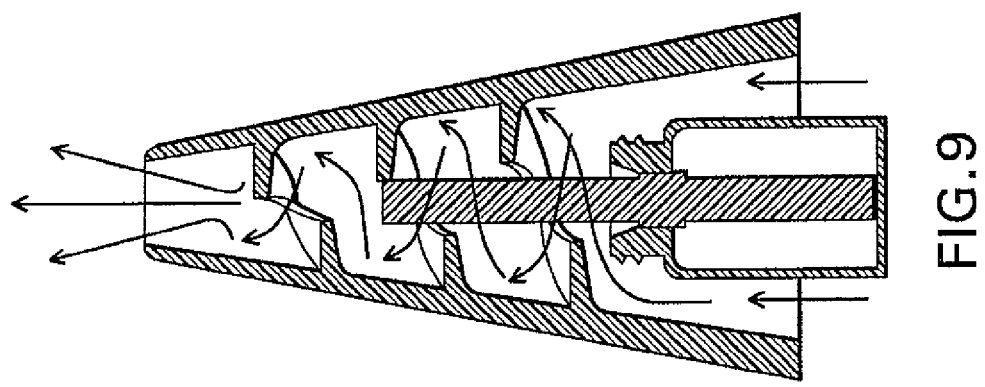
FIG. 9 is an interior view of a plug-in version having a helical baffle that efficiently provides air flow around the wick.
Figure 10:
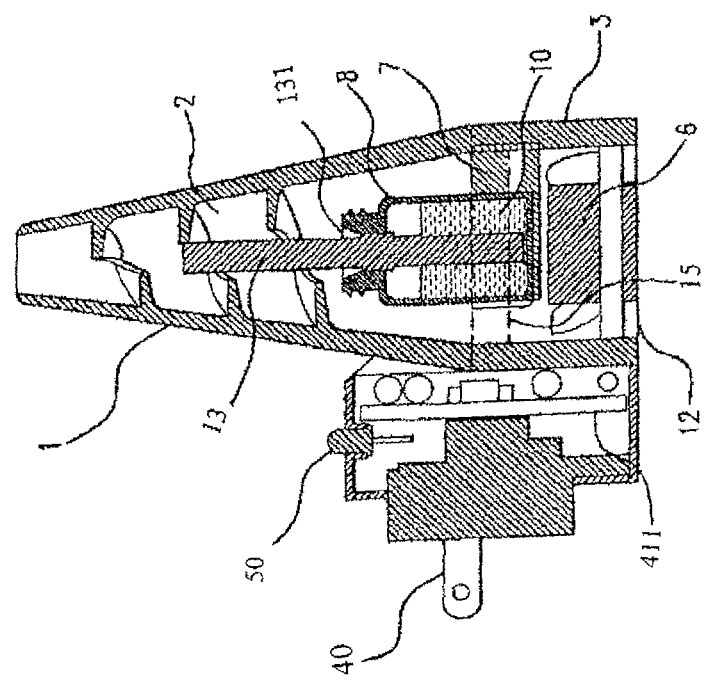
FIG. 10 is profile view of a "plug-in" embodiment of the present application.
Figure 11:
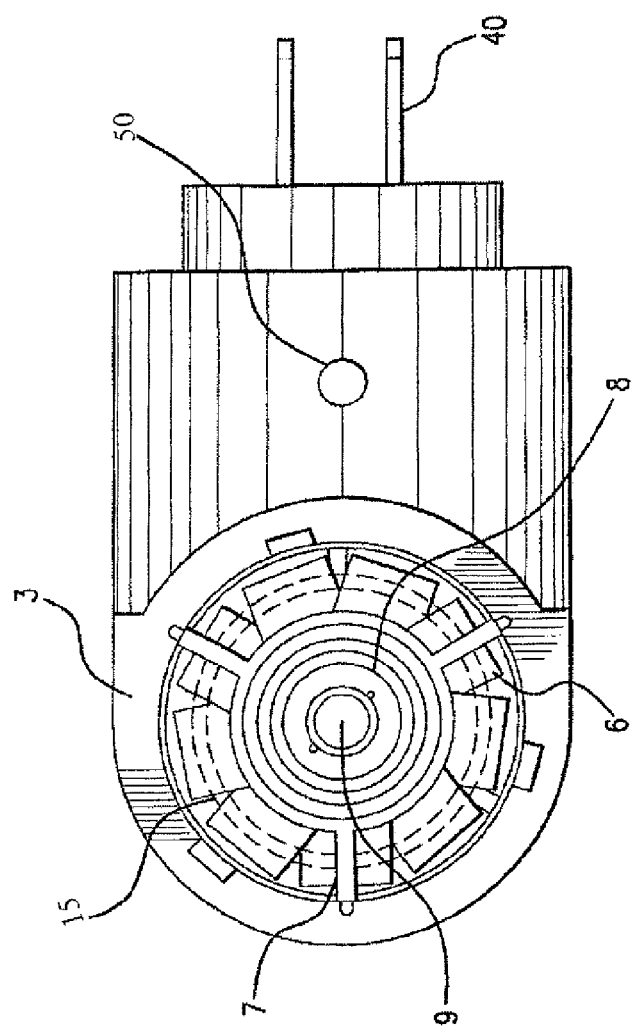
FIG. 11 is a birds'-eye view of this embodiment.

An example of a "plug-in" embodiment is shown in FIG. 8, which includes AC wall outlet 40 as a power source and contains a power supply mounted on control circuit board 411 to provide safety, control circuit board 411 shown in FIG. 10, bi-color light emitting diode (LED) 50, fan 6, fragrance supply bottle (bottle can be optionally configured with an orientation key or having a variety of shapes) 8. FIGS. 10 and 11 show, respectively, the profile and birds-eye views of a plug-in embodiment of the present application.

In preferred embodiments, the liquid-evaporate delivery device may be constructed with an air exchange/liquid collection vent 131 as shown in FIG. 10. In the delivery device shown in FIG. 10 the fragrance supply bottle support mount contains a bottle sensor 7, (optionally configured with a mating orientation key or accepting a variety of bottle shapes). Air tunnel 11 is provided within item 3 as shown in FIG. 8.

As explained above and with reference to FIGS. 10 and 11, the optional strip heater 15, could be configured to operate specific to the fragrance bottle orientation or key. This feature would permit the application of heat to a viscous or semisolid liquid mixture to be pre-determined at the point of manufacture. Hence, the physical properties of the bottle contents would determine the bottle shape or key setting for the application of ambient, warm or hot air to the supply bottle and wick.

It should be understood by those skilled in the art that the aero-dynamic enclosure, items 2 and 3 can be any of a number of designs and shapes, and is not limited to that which is illustrated in the Figures of this application (e.g. as shown in FIGS. 2, 4 and 5). The enclosure may be constructed of any suitable material such as: plastic, glass, metal, ceramic, etc. The device may be configured to provide a helical air flow that provides from about 1 to about 5 wraps around the wick, or from about 2 to 3 wraps around the wick by a one-piece spiral design (e.g. as shown in FIG. 6).

With reference to FIG. 10, the construction of the fragrance supply bottle 8 is preferably such that it can be handled without spilling the fragrance 10 contained therein. When the fragrance 10 has dissipated, the fragrance supply bottle 8 is replaced and a new fragrance supply bottle is simply inserted into the fragrance supply bottle support mount 7.

It is understood that replacement liquid supply bottles (e.g. fragrance supply bottles) that are designed to be used in the liquid-evaporate delivery devices of the present invention are also intended to be included within the inventive subject matter of the present application. Accordingly, one embodiment of the present application provides a kit comprising a liquid supply bottle that may be used in the devices of the present application, the kit further comprising instructions to insert or otherwise employ the liquid supply bottle in any of the devices described in this application.

The device can also be envisioned to have a variety of delivery rates dependent on the on/off sequence, fan speed, application of heat and additional features controlled by the micro-controller. With reference to FIG. 10, a micro-controller, located on the control circuit board 411, is connected to the fan 6 and drives the fan at a predetermined time-on and time-off sequence. Adjusting the predetermined time-on and time-off sequence of the fan 6 permits control of the amount of fragrance delivered into the atmosphere. This feature affords the consumer considerable flexibility with regards to room size and delivery rate preference. In addition, the micro-controller can be optionally configured with trigger devices, such as, infra-red motion entry sensors, light detectors, door opening detectors, malodor sensors, etc. To one skilled in the art of designing such features, the opportunities are numerous.

In various embodiments, various pitches of the helix, one of which shown in FIG. 2 as 16, may be provided. The helix orientation may be determined by a person of ordinary skill in the art depending on various factors, including the size of the device, the intended space in which the liquid-evaporate delivery device will operate (e.g. the size of the room), and the type and characteristics of the liquid to be employed in the device (e.g. the volatility of the fragrance).

Referring again to FIG. 2, the liquid-evaporate delivery device may be provided with an optional strip heater 15, shown in this embodiment to be in close proximity to fragrance supply bottle 12. The strip heater may optionally be in communication with a circuit board 7 and receive input based on the shape of the fragrance supply bottle, which is also in communication with the circuit board 7. In such an embodiment, the amount of heat to be delivered to the liquid-evaporate delivery device may be optimized based on the liquid (e.g. fragrance) applied, the fragrance being provided in a fragrance supply bottle with a distinct shape that provides the correct amount of heat supplied, based on the characteristics of the fragrance.

Operating conditions for the fan in both the plug-in and battery operated embodiments can be determined by persons of ordinary skill in the art. In one embodiment the fan operates continuously at, for example a range from about 500 r.p.m. to about 1500 r.p.m. (e.g. about 900 or 1000 r.p.m.). Furthermore, the fan may operate on a timer or motion-detector sensor so that the fan runs intermittently at pre-selected intervals or when offensive odors are detected by the device (e.g. in bathroom applications). Sensors for detecting odors are known in the art, and can be integrated with the liquid-evaporate delivery device by persons of ordinary skill in the art.

Liquids

In a preferred embodiment, the liquid-evaporate delivery device delivers a fragrance composition. The fragrance compositions that may be used include commercially available fragrances, such as fragrances available from Takasago International Corporation U.S.A., (Rockleigh, N.J.) is preferred. Other sources of liquid or gel fragrance compositions include S.C. Johnson Company (Racine, Wis.), Procter & Gamble (Cincinnati, Ohio), Reckitt Benckiser (Berkshire, UK), Givaudan (Geneva, Switzerland), Firmenich (Geneva, Switzerland), Symrise (Holzminden, Germany), Henkel/Dial (Düsseldorf, Germany) and International Flavors and Fragrances (New York, N.Y.).

Also, malodor control compositions may be used in the liquid-evaporate delivery device of the present application, either alone or in combination with a fragrance composition. Accordingly, the liquid-evaporate delivery device may be used to neutralize and/or control odors, instead of, or in addition to, providing a hedonically pleasing odor to the surrounding air space. Use of malodor control compositions may find utility in bathroom and kitchen applications, and other areas in which malodors are likely to be present. For example, the malodor control compositions disclosed in U.S. Pat. No. 6,660,713 (assigned to Procter & Gamble), hereby incorporated by reference, could be used in the liquid-evaporate delivery device of the present application.

An advantage of the liquid-evaporate delivery device is that, by more efficient use of air currents, the performance of the device can be improved. This could mean that the use of a heater can be optional and contingent on the desired evaporative delivery. Accordingly, fragrance can be evaporated while minimizing or eliminating fractionation of individual components, thus providing a wider range of notes available to the perfumer when selecting liquid fragrance compositions to be used in devices of the present application.

The liquid-evaporate delivery device may also deliver insecticides or insect repellents. Insect repellents and insecticides known to those of ordinary skill in the art may be used, such as the active ingredients described in U.S. Published Application No. 2006/0083763, which is hereby incorporated by reference in its entirety. Preferred insect repellent compositions include insect repellent compositions containing para-menthane diol, commercially available from Takasago International Corporation U.S.A. (Rockleigh, N.J.).

As discussed above, the liquid-evaporate delivery device may be configured to provide specific heat input and/or fan speed inputs based on the shape of the fragrance supply bottle. For example, fragrance compositions having a higher percentage of lower, more subtle notes may be provided with additional heat supply and/or increased fan speed. The liquid-evaporate delivery device may recognize use of a lower note-dominate fragrance based on the particular shape of the fragrance supply bottle (e.g. by use of a square bottle). Alternatively, more volatile fragrance compositions that do not require as much heat and/or fan speed may be provided in a different shaped fragrance supply bottle (e.g. a triangular shaped fragrance supply bottle) that is recognized by the device to lower the fan speed and/or lower the amount of applied heat.

Gels could also be used in the liquid-evaporate delivery device of the present application. The gels could be, for example, fragrance gels or therapeutic gel (e.g. aloe vera gel, essential oil gels).

Uses

The liquid-evaporate delivery device of the present application may be applied to household rooms and used as an air freshener. Alternatively, the liquid-evaporate delivery device may be used in an office environment (e.g. at reception areas), or a place of business (e.g. a reception area) or a place of recreation (e.g. a casino).

Alternatively the liquid-evaporate delivery device can be used as a means to control insects and nuisance pests. The liquid applied to the liquid-evaporate delivery device could be an insect repellent composition. Accordingly, the liquid-evaporate delivery device could be used on decks, pavilions, stadiums, outdoor dining facilities and other places where people congregate outdoors or indoors and it is desired to repel insects.

Another use for the liquid-evaporate delivery device of the present invention is to deliver therapeutic agents (e.g. therapeutic gels) to a human via an inhalation route, including medicinal, holistic and homeopathic compositions that may be vaporized for inhalation. For example, the liquid-evaporate delivery device may deliver essential oils or medicated gels (e.g. Vicks® VapoRub® Products, commercially available from Procter & Gamble and Co. (Cincinnati, Ohio).

In one therapeutic application of the present invention, the liquid-evaporate delivery device is charged with essential oil(s) and provided in close proximity to a subject such that the subject inhales gas or vapors from the essential oil(s). It has been found that essential oils, such as cinnamon bark, lemongrass and thyme oils, provide antibacterial activity when inhaled and may be used to treat, for example, respiratory tract infections. See, Journal of Antimicrobial Chemotherapy, 47:565-573 (2001), which is hereby incorporated by reference in its entirety. There it was concluded that the antimicrobial action of essential oils by gaseous inhalation is most efficient at high vapour concentration for a short time, and that a maximal vapour level of 0.1-0.9 mg/L in air may suppress the growth of the bacterial pathogens of respiratory infection (e.g. *Haemophilus influenzae, Streptococcus pneumoniae, Streptococcus pyogenes* and *Staphyloccoccus aureaus*). The essential oils that may be used in therapeutic applications (e.g. treatment of respiratory tract infections) in the device of the present application may be selected from, for example, cinnamon bark oil, lemongrass oil, thyme oil (wild), thyme oil (red), thyme oil (geraniol), perilla oil, peppermint oil, tea tree oil, coriander oil, lavender (spike) oil, lavender (true) oil, rosemary oil, eucalyptus (radiata) oil, citron oil, and mixtures thereof. Alternatively, the major active constituents of the essential could be used in place of, or in addition to, the essential oil (e.g. cinnamaldehyde, neral, geranial, limonene, perillaldehyde, carvacrol, limonene, γ-terpinene, thymol, geraniol, geranyl acetate, p-menthone, menthol, terpinen-4-ol, linalool, 1,8-cineole, camphor, linalyl acetate, α-pinene, and α-terpineol).

It shall be understood that while a fan is described in some embodiments of the present application, the invention is not limited thereto. So long as the device receives sufficient wind flow—including many if not most embodiments that employ the device outside—a fan would not be required, or could be provided only as an alternative when ambient air supply is not sufficient. In some embodiments, sufficient wind flow is already provided that totally obviates the fan. The liquid-evaporate delivery device of the present invention can be used without a fan, for example, in air vents, cars, boats, all-terrain vehicles and outdoor areas that tend to be windy (e.g. tunnels). A person of ordinary skill can determine whether a fan is required when optimizing the liquid-evaporate delivery device for the particular application.

A person of ordinary skill in the art may modify the liquid-evaporate delivery device to an alternative configuration or size based on the application for which it is used. For example, in car interior applications, the device could be made smaller and adapted to securely fit in the vent within the interior passenger space of the car. The person of ordinary skill can select higher fan speeds and/or provide additional heat to formulations when it is required to deliver more evaporate, such as when using the device for insect control purposes or when delivering a more-subtle fragrance.

EXAMPLE 1

Prototype tabletop units were tested for liquid weight loss to determine the technical attributes of the unit while periodic hedonic evaluations were made of the fragrance strength. Tests were performed to estimate the use life of the unit with a fixed amount of fragrance, based on average weight loss of the fragrance.

Testing occurred in a climate controlled room where temperature, humidity, air flow and voltage are consistent and monitored. The temperature of the room is controlled at 70° F.+/−1°, humidity is 50%+/−10%; air flow is maximum 10 cubic feet per minute face value; and the voltage is 120+/−1 volts.

Both the controls and the inventive liquid-evaporate delivery devices are electrical. The inventive units do not supply heat to the evaporating wick while the controls do increase the evaporating rate by the use of a heating element near the wick in their units.

A device generally depicted in FIG. 2 was tested. The reservoir bottles were filled with 12 grams of one of four fragrances (tropical A, tropical B, floral, and fresh fragrance) and testing was complete when there was no visual liquid fragrance remaining even though the wick might contain 2-3 grams of fragrance. The inventive units of the present application were tested in the continuous on mode to determine the weight loss per day and for charting purposes, the units were weighed frequently with 3 readings per week for the first two weeks and then 2 readings per week until the unit was visually empty.

As controls, a plug-in heated wick with a bottle reservoir and without a fan was tested. An example of such a device include commercial products available S.C. Johnson "Glade® Plug-In® Scented Oil" product, Procter and Gamble "Febreze® Noticeables™" product and Reckitt Benckiser Air Wick® (PISO) unit.

The weight loss of fragrance per day is set forth below in Table 1.

TABLE 1

| Device | Fragrance Tested | Average weight loss per day (mg/day) |
|---|---|---|
| Device of Present Application | Tropical A | 353 |
| Comparative Commercial Embodiment 1 | Tropical A | 400 |

TABLE 1-continued

| Device | Fragrance Tested | Average weight loss per day (mg/day) |
|---|---|---|
| Device of Present Application | Fresh | 353 |
| Comparative Commercial Embodiment 2 | Fresh | 547 |
| Device of Present Application | Floral | 148 |
| Comparative Commercial Embodiment 3 | Floral | 665 |
| Device of Present Application | Tropical B | 191 |

The results are also shown graphically in FIG. 12. Based on the average weight loss per day, the devices of the present application are predicted to have a longevity of about 1 to 2 months.

The results demonstrate that the liquid-evaporate delivery devices of the present application can yield amounts of fragrance comparable to devices that employ heat to help facilitate evaporation. It is understood that so long as the device, depending on room size, delivers about 100 to 800 mg/day, a hedonically pleasing result can be obtained. As shown in FIG. 11, and most importantly, the devices of the present application also yield a relatively constant amount of fragrance over a period of about 20 days. Furthermore, the quality and character of the fragrance, i.e. the smell perceived by the user, was substantially the same over the period tested.

EXAMPLE 2

The longevity of fragrance emissions over 28 days using a device shown generally in FIG. 2 was compared to commercially available units described in Example 1. A tropical fragrance, a fresh fragrance and a floral fragrance were tested. The devices were left on continuously for 28 days or 35 days and the strength of smell was evaluated by evaluators skilled in the fragrance art on a scale of 1 (weak) to 5 (strong). The device of the present application was charged with 12 grams of fragrance and the control devices were charged with between 20 and 26 grams of fragrance.

The results of the longevity analysis are shown below in Table 2:

TABLE 2

| Device/Fragrance | Initial (Day 0) | Day 7 | Day 14 | Day 21 | Day 28 | Day 35 |
|---|---|---|---|---|---|---|
| Device of Present Application/ Fresh (12 g) | 5 | 5 | 5 | 4.5 | 4.5 | 4.5 |
| Comparative Commercial Embodiment 1/ Fresh (20.5 g) | 5 | 5 | 5 | 4.5 | 4 | 3.5 |
| Comparative Commercial Embodiment 2/ Fresh (26 g) | 5 | 5 | 5 | 4.5 | 4.5 | 4 |
| Device of Present Application/ Tropical (12 g) | 5 | 5 | 5 | 5 | 5 | NA |
| Comparative Commercial Embodiment 1/ Tropical (20.5 g) | 5 | 5 | 4.5 | 4.5 | 4.5 | NA |
| Comparative Commercial Embodiment 2/ Tropical (26 g) | 5 | 5 | 5 | 5 | 5 | NA |

TABLE 2-continued

| Device/Fragrance | Initial (Day 0) | Day 7 | Day 14 | Day 21 | Day 28 | Day 35 |
|---|---|---|---|---|---|---|
| Device of Present Application/ Floral (12 g) | 5 | 5 | 4.5 | 4.5 | 4.5 | 4.5 |
| Comparative Commercial Embodiment 1/ Floral (20.5 g) | 5 | 5 | 4 | 3 | 2.5 | 3 |
| Comparative Commercial Embodiment 1/ Floral (26 g) | 5 | 5 | 4 | 4.5 | 4 | 4 |

As shown in Table 2, each device tested emitted a strong fragrance for the first 14 days of operation. At day 21 onward, however, the device of the present application performed as well as, or better than commercially available devices that were initially loaded with more fragrance. The example demonstrates that the device of the present application is more efficient at delivering a unit amount of fragrance to the ambient air.

* * * *

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

The invention claimed is:

1. A liquid-evaporate delivery device comprising:
(a) a container containing at least one substance to be evaporated;
(b) a wick having a first end, a second end and an exterior surface, the first end disposed within the container and the second end and exterior surface disposed exterior to the container;
(c) an air flow device configured to impart an air flow on the wick; and
(d) a housing having a helical channel, wherein the housing houses the container, the wick, and the air flow device, wherein the air flow device is configured to impart the air flow within the housing;
wherein the helical channel circulates the air flow around the exterior surface of the wick.

2. The liquid-evaporate delivery device of claim 1, wherein the at least one substance is selected from a fragrance, an essential oil, a malodor control composition, a therapeutic gel, a therapeutic liquid, an insecticide or an insect repellent or pest repellent, or any combination thereof.

3. The liquid-evaporate delivery device of claim 1, wherein the at least one substance is a fragrance.

4. The liquid-evaporate delivery device of claim 3, wherein the liquid-evaporate delivery device delivers a substantially uniform amount of the fragrance each day over a period of at least 30 days.

5. The liquid-evaporate delivery device of claim 1, wherein the air flow device is a fan.

6. The liquid-evaporate delivery device of claim 5, wherein the fan is aligned with a central axis of the wick.

7. The liquid-evaporate delivery device of claim 1, wherein the air flow is substantially laminar.

8. The liquid-evaporate delivery device of claim 1, wherein the wick is selected from a nylon, a linen, a felt, a rayon, a polyamide, a polymer, a polypropylene polymer, a polyethylene polymer, polyester fibers, cellulose acetate fibers, ceramic, sintered glass, glass fibers, a plastic, a cotton, a cellulose or mixtures thereof.

9. The liquid-evaporate delivery device of claim 1, wherein the housing further includes at least one baffle the defines the helical channel, wherein the helical channel circulates the air flow around the exterior surface of the wick.

10. The liquid-evaporate delivery device of claim 9, wherein a central axis of the wick is concentric with a central axis of the helical channel.

11. The liquid-evaporate delivery device of claim 9, wherein the at least one baffle includes a first and a second baffle, wherein the helical channel is provided by the first and second baffles.

12. The liquid-evaporate delivery device of claim 1, further comprising a replacement container containing at least one substance to be evaporated, wherein the container is removed from the housing and the replacement container is inserted therein.

13. The liquid-evaporate delivery device of claim 1, wherein the at least one substance includes at least one of an essential oil or a major constituent of an essential oil.

14. The liquid-evaporate delivery device of claim 1, further comprising a heater element operatively engaged with the container.

15. A method of providing fragrance to an air space, comprising:
providing a liquid-evaporate delivery device the device including
(a) a container containing at least one substance to be evaporated,
(b) a wick having a first end, a second end and an exterior surface, the first end disposed within the container and the second end and exterior surface disposed exterior to the container,
(c) an air flow device configured to impart an air flow on the wick, and
(d) a housing to house the container, the wick, and the air flow device, wherein the air flow device is configured to impart the air flow within the housing, the housing having a helical channel; and
imparting air flow by the air flow device within the housing to rotate the air flow around the exterior surface of the wick via the helical channel.

16. A liquid-evaporate delivery device comprising:
(a) a retention member containing at least one substance to be evaporated;
(b) an evaporation member operatively engaged with the retention member;
(c) a fan configured to impart air flow on the evaporation member;
(d) a housing, wherein the retention member, evaporation member, and fan are disposed within the housing;
wherein the housing includes at least one baffle that defines a helical channel for directing air flow around an exterior surface of the evaporation member.

17. The liquid-evaporate delivery device of claim 16, wherein the at least one substance comprises a liquid, wherein the evaporation member comprises a wick in communication with the liquid disposed in the retention member.

18. The liquid-evaporate delivery device of claim 17, wherein the liquid is a fragrance composition.

19. The liquid-evaporate delivery device of claim 16, wherein the air flow is substantially laminar.

20. A liquid-evaporate delivery device kit comprising
(a) a bottle containing at least one substance to be evaporated;
(b) a wick, the wick having a longitudinal axis defined by a lower portion disposed within the bottle and an upper portion protruding from the bottle, the wick configured to draw the substance to be evaporated with the lower portion from the bottle toward the upper portion of the wick;
(c) a fan having a central axis; and
(d) a housing includes a helical channel, wherein the housing retains the bottle and the fan;
wherein the longitudinal axis of the wick is aligned with the central axis of the fan and the helical channel circulates air helically around an exterior surface of the wick.

21. The liquid-evaporate delivery device kit of claim 20, wherein the at least one substance is a liquid fragrance composition.

22. The liquid-evaporate delivery device kit of claim 21, wherein the liquid-evaporate delivery device delivers a substantially uniform amount of fragrance each day over a period of at least 30 days.

23. The liquid-evaporate delivery device kit of claim 20, further comprising a replacement container containing at least one substance to be evaporated.

* * * * *